United States Patent [19]

Horodysky et al.

[11] 4,301,019

[45] Nov. 17, 1981

[54] MERCAPTOTHIADIAZOLE ADDUCTS OF UNSATURATED ESTERS AND LUBRICANTS CONTAINING SAME

[75] Inventors: Andrew G. Horodysky, Cherry Hill; Phillip S. Landis, Woodbury, both of N.J.

[73] Assignee: Mobil Oil Corporation, New York, N.Y.

[21] Appl. No.: 201,885

[22] Filed: Oct. 29, 1980

[51] Int. Cl.$^3$ .............................................. C10M 1/10
[52] U.S. Cl. .................................. 252/49.6; 252/47.5; 548/110; 548/141; 548/142
[58] Field of Search ........................... 252/47.5, 49.6; 548/110, 141, 142

[56] References Cited

U.S. PATENT DOCUMENTS

| | | | |
|---|---|---|---|
| 2,611,744 | 9/1952 | Kipp | 252/49.6 |
| 2,760,933 | 8/1956 | Fields et al. | 548/142 X |
| 2,836,564 | 5/1958 | Roberts et al. | 252/47.5 |
| 3,150,157 | 9/1964 | Liao | 252/49.6 X |
| 3,505,226 | 4/1970 | Cyba | 252/49.6 |
| 3,519,564 | 7/1970 | Vogel | 252/47.5 |
| 4,097,387 | 6/1978 | Caspari | 252/47.5 |
| 4,104,179 | 8/1978 | Colclough | 252/47.5 X |
| 4,136,043 | 1/1979 | Davis | 252/47.5 |
| 4,140,643 | 2/1979 | Davis | 252/47.5 |
| 4,193,882 | 3/1980 | Gemmill, Jr. | 252/47.5 |

FOREIGN PATENT DOCUMENTS

| | | | |
|---|---|---|---|
| 799055 | 7/1958 | United Kingdom | 252/47.5 |
| 1377433 | 12/1974 | United Kingdom | 548/142 |

*Primary Examiner*—Andrew Metz
*Attorney, Agent, or Firm*—Charles A. Huggett; Michael G. Gilman; Claude E. Setliff

[57] ABSTRACT

Mercaptothiadiazole is reacted with hydroxyl-containing unsaturated esters, or their borated derivatives, to yield a product that is useful as a friction reducing additive in lubricants.

26 Claims, No Drawings

4,301,019

MERCAPTOTHIADIAZOLE ADDUCTS OF UNSATURATED ESTERS AND LUBRICANTS CONTAINING SAME

BACKGROUND OF THE INVENTION

1. Field of the Invention

The invention is concerned with hydroxyl-containing unsaturated esters or the borated derivatives thereof, that have been reacted with a mercaptothiadiazole. It also relates to lubricant compositions containing same.

2. Discussion of the Prior Art

Efforts to reduce the amount of fuel consumed by lubricated equipment and the like have accelerated in recent years having been given added impetus by the oil embargo. Many of the solutions have been strictly mechanical, but other efforts have revolved around finding lubricants that reduce the overall friction in the lubricated equipment, thus allowing a reduction in energy requirements thereto. Much work has been done with mineral lubricating oils and greases, modifying them with additives to reduce their friction properties. On the other hand, new lubricants have been synthesized and compounded for use in modern engines. Among these are the synthetic lubricating oils, which are known to reduce fuel consumption by a significant amount.

So far as is known, no effort has been made to employ the mercaptothiadiazole adducts of hydroxyl-containing acid esters or borated hydroxyl-containing esters as a lubricant additive. U.S. Pat. No. 2,788,326 discloses some of the starting esters suitable for the present invention, e.g. glycerol monooleate, as minor components of lubricating oil compositions. U.S. Pat. No. 3,235,498 discloses, among others, the same ester as just mentioned, as an additive to other oils. U.S. Pat. No. 2,443,578 teaches esters wherein the free hydroxyl is found in the acid portion, as for example in tartaric acid.

Other patents, such as U.S. Pat. Nos. 2,798,083; 2,820,014; 3,115,519; 3,282,971; and 3,309,318, as well as an article by R. S. Barnes et al, entitled "Synthetic Ester Lubricants" in Lubrication Engineering, Aug., 1957, pp. 454-457, teach lubricants prepared from polyhydric alcohols and acid containing no hydroxyl other than those associated with the acid function. However, all these references teach lubricants prepared from the fully esterified material.

SUMMARY OF THE INVENTION

The invention provides a lubricant composition comprising a major amount of a lubricant and an anti-friction amount of a mercaptothiadiazole adduct of a hydroxyl-containing unsaturated ester or borated derivative thereof. The invention also provides the adduct as a new composition of matter.

DESCRIPTION OF THE SPECIFIC EMBODIMENTS

The modern automobile traveling at speeds as low as 40 mph has available to it for propelling the vehicle only about 13% of the potential energy in a gallon of gasoline. A large part of this loss, or about 5%, is lost because of internal friction in the engine. Obviously, one way to boost fuel economy is to cut this friction loss.

The present invention minimizes such friction losses and thereby decreases fuel consumption for a given distance traveled by employing ester adducts, or mixtures of ester adducts, as lubricating components of lubricating oils. The products of the present invention are relatively non-corrosive to copper and may actually serve to improve the copper strip corrosivity of normally corrosive lubricants. This improvement in copper strip corrosivity may be derived from the thiadiazole moiety of the adduct. In this regard, it has been discovered that a particular class of esters is useful for the purpose. These contain a free hydroxyl group, derived either from the polyhydric alcohol or from the acid. When the alcohol is used as the source of free hydroxyl, it is necessary that the reaction mixture contain less acid than is stoichiometrically equivalent to the number of hydroxyls present in said alcohol. On the other hand, if the free hydroxyl is found in the acid, the alcohol may be fully reacted with the acid carboxyls.

Typical polyhydric alcohols (which term includes glycols, etc.) contemplated for use in this invention include those containing from 2 to 30 carbon atoms and from 2 to 6 hydroxyls. Specific members that may be mentioned are the alkylene glycols, particularly ethylene glycol and propylene glycol; the diglycols, glycerol; sorbitan, the trimethylolalkanes, such as trimethylolopropane; neopentyl glycol; pentaerythritol; dipentaerythritol; the polyalkyl alkane diols such as 2,2-dimethyl-3-isopropyl-1, 3 propanediol; and the like.

The acids useful as reactants with these alcohols include any unsaturated monocarboxylic acid of the formula:

R—COOH wherein R is a straight or branched chain alkenyl group containing from 2 to 30 carbon atoms or mixtures thereof, but no alcoholic hydroxyl group. A particularly effective acid, or acid mixture, may be found among those having from 3 to 31 carbon atoms. Some of the acids that may be named are propenoic, butenoic, pentenoic, hexenoic, octenoic, dodecenoic, octadecenoic (oleic) acid and lineoleic acids. Among the esters contemplated in this class are diglycol oleate, glycerol mono- and dioleate and the like.

They also include unsaturated hydroxyl-containing acids of the formula:

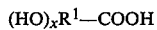

(HO)$_x$R$^1$—COOH wherein R$^1$ is a straight or branched chain alkenylene group containing 2 to 30 carbon atoms or mixtures thereof.

The esters can be made by methods well known in the art. In general, they are made by mixing the acid and alcohol in the desired ratio and heating at from 100° C. to 250° C., depending upon the molecular size of the reactants, for from 1 to 20 (hours). There is gnerally no need for purification, except perhaps for the removal of unreacted reactants, and the product can be used as made.

At least one or more olefinic groups must be present in the hydroxyl-containing ester or borated hydroxyl-containing ester. More are permissible. A hydrocarbyl chain may contain two or more olefinic groups. The number of ester groups present in the hydroxyl-containing or borated hydroxyl-containing unsaturated ester reactant generally should not exceed four. It is also important that the ester reactant contain a hydrocarbon chain of 12 or more carbon atoms.

Without limiting the types of hydroxyl-containing esters, those that might be mentioned include ethylene glycol monooleate, propylene glycol monooleate, butanediol monooleate, butanediol monolinoleate, glycerol monooleate, glycerol dioleate, glycerol monomyristate monooleate, pentaerythritol dioleate, pentaerythritol dioleate monoproprionate, pentaerythritol monooleate dimyristate, pentaerythritol trioleate, pentaerythritol monomyristate dioleate, trimethylolpropane dioleate, trimethylolpropane dilineoleate, trimethylolpropane monooleate and mixtures thereof. Where mixed acids are used, one or more should have 12 carbon atoms or more to improve oil solubility.

The borated intermediates of the present invention are produced by the reaction of the hydroxyester with boric acid in a suitable solvent or solvents such as toluene, xylene, or reactive solvents, at temperatures ranging from about 90° C. to about 250° C. to yield products containing at least 0.01% or more of boron. Specific reaction conditions and molar equivalents of the reactants are well known in the art. Partial or complete boration can be used to impart the beneficial characteristics. In carrying out the reaction, an excess of a boron-containing borating reagent can be used for more complete boration which is generally preferred. Boration is not limited to the boric acid method, however, and any convenient method of boration known to the art may be used.

For example, transesterification using a trialkyl borate such as tributyl borate at reaction temperatures up to 270° C. can be used. Broadly, also useful are the alkyl borates of the formula $$(R^2O)_aB(OH)_b$$

wherein $R^2$ is a $C_1$-$C_6$ alkyl group, a is 1 to 3 and b is 0 to 2. When this reactant is used, the final ester borate product can be illustrated as:

$$[-O]_mB(OH)_n$$

where m is 3 and n is 0, when three moles of hydroxyester are reacted with one mole of the boron compound and the reaction is carried to completion. However, when less than a stoichiometric amount of hydroxyl-containing unsaturated ester is present for reaction, the boron will still have attached thereto one or more —OR groups or one or more —OH groups, depending upon which of such groups react. That is to say, the product may be terminated in one of the following ways:

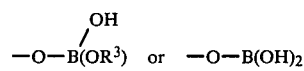

In carrying out the reaction to form the boron product, up to stoichiometric amounts of the hydroxyester and boron compound may be used. That is, for every one mole of boron compound, one may use up to an amount of the hydroxyester which will contain an equivalent amount of hydroxyl functions. The temperature of reaction can vary over the range of from about 75° C. to about 270° C., preferably from about 100° C. to about 200° C.

While atmospheric pressure is generally preferred, the reaction with the boron compound can be advantageously run at from about 0.3 to about 2 atmospheres. Furthermore, a solvent is desirable. In general, any polar or non-polar, unreactive solvent can be used, including toluene, xylene, 1, 4-dioxane or reaction solvents such as butanol, pentanols, etc. Times for completing the reaction will range from 1 to 20 hours.

Some of the thiadiazoles useful in the practice of this invention are more particularly called mercaptothiadiazoles, and can include 2,5-dimercapto-1,3,4-thiadiazole and have the formula:

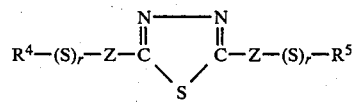

wherein $R^4$ and $R^5$ are hydrogen or hydrocarbyl groups, containing from 1 to 30 carbon atoms, r is to 0 to 3 and Z is nitrogen or sulfur, one of which must be sulfur. The hydrocarbyl groups can be alkyl, aryl, alkenyl alkaryl or aralkyl preferably alkyl, and specifically include methyl, butyl, octyl, decyl, dodecyl, octadecyl, phenyl, tolyl, benzyl, and the like. One of $R^4$ and $R^5$ must be hydrogen. They can be made in accordance with the method described in U.S. Pat. No. 2,719,125, which is incorporated herein by reference. It may also be purchased from commercial sources.

The mercaptothiadiazoles useful herein also include amino derivatives such as

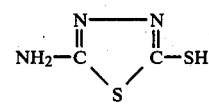

The synthesis and structure of the mercaptothiadiazole hydroxyl-containing unsaturated ester may be depicted by the following general equations:

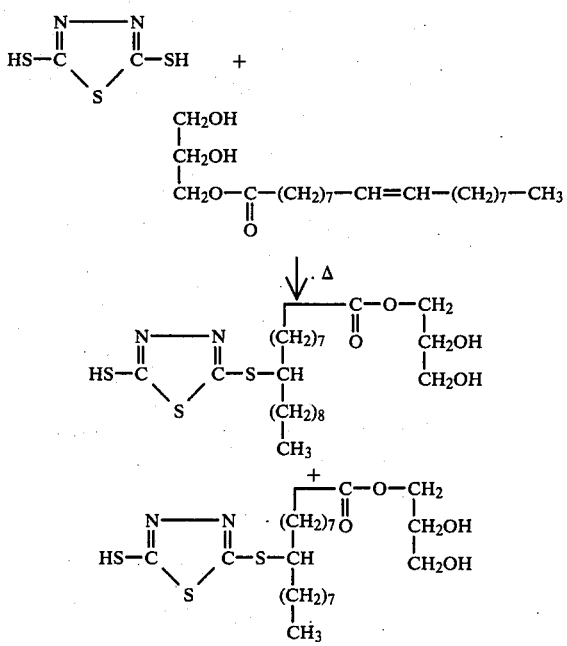

The above equations depict the simplest reaction of glycerol monooleate with 2,5-dimercapto-1,3,4-thiadiazole. It is equally possible for the second mercapto group of the thiadiazole to also add across the double bond of another unsaturated moiety. In the case of glycerol dioleate, the mercaptan groups can add across both double bonds. In this case oligomers and mixed products are possible. Mixtures of hydroxyl-containing unsaturated esters can also be used.

Statistical mixtures including products derived from the reaction of more than one olefin group per molecule are possible. The reaction of both mercapto groups of 2,5-dimercapto-1,3,4-thiadiazole is also quite possible and is dependent primarily upon the molar ratio of the reactants used. Thus, although we believe the reactions as indicated predominate, other reactions are possible. We do not wish to be bound to the chemistry shown since other products may form in lesser amounts.

The above general equations and considerations are equally valid with respect to the reaction of mercaptothiadiazoles with borated hydroxyl-containing unsaturated esters, mixtures of borated hydroxyl-containing unsaturated esters, mixtures of hydroxyl-containing unsaturated esters and borated hydroxyl-containing unsaturated esters.

Reaction temperatures may range from about 140° C. to about 200° C. The pressure is usually atmospheric, but lighter pressure maybe used, if desired. An inert gas purge is often used to minimize possible decomposition.

Equimolar amounts of reactants are used. However, the molar ratio of hydroxyl-containing or borated hydroxyl-containing unsaturated ester to mercaptothiadiazole may vary from more than 2:1 to less than 1:2. A large excess of hydroxyl-containing or borated hydroxyl-containing unsaturated ester can be also used with molar ratios in excess of two-fold. Although this reaction is generally carried out at elevated temperatures, acid catalysts or peroxide catalysts may be used to effect the reaction at lower temperatures. Hydrocarbon solvents could be optionally used, but are not required.

The boron compound can be used in amounts stoichiometric to the hydroxyl present in the hydroxyl-containing ester or, if preferred, less than stoichiometric amounts can be used so free hydroxyl groups are present in the final product.

The additives may be used effectively to impart to organic media, particularly to greases and lubricating oils, the properties mentioned hereinabove. An effective amount of the additive compound will range from about 0.1% to about 10% by weight. Preferably the organic medium or substrate, e.g., oil of lubricating viscosity or grease therefrom, contains from about 1.0% to 5.0% of the additive and more preferably from about 2.0% to about 4.0% by weight thereof, based on the total weight of the lubricant composition.

Of particular significance, in accordance with the present invention, is the ability to improve the resistance to oxidation and corrosion of oleaginous materials such as lubricating media which may comprise liquid oils, in the form of either a mineral oil or a synthetic oil, or in the form of a grease in which any of the aforementioned oils are employed as a vehicle. In general, mineral oils, both paraffinic, naphthenic and mixtures thereof, employed as the lubricant, or grease vehicle, may be of any suitable lubricating viscosity range, as for example, from about 45 SUS at 100° F. to about 600 SUS at 100° F., and preferably, from about 40 SUS to about 250 SUS at 210° F. These oils may have viscosity indexes ranging to about 100 or higher. Viscosity indexes from about 70 to about 95 are preferred. The average molecular weights of these oils may range from about 250 to 800. Where the lubricant is to be employed in the form of a grease, the lubricating oil is generally employed in an amount sufficient to balance the total grease composition, after accounting for the desired quantity of the thickening agent and other additive components to be included in the grease formulation. A wide variety of material may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which are normally employed for thickening or gelling hydrocarbon fluids for forming grease can be used in preparing the aforementioned improved grease in accordance with the present invention.

In instances where synthetic oils, or synthetic oils employed as the vehicle for the grease, are desired in preference to mineral oils, or in combination therewith, various compounds of this type may be successfully utilized. These synthetic oils may be used alone, in combination with mineral oils, or with each other as a lubricating oil. Typical synthetic vehicles include synthetic hydrocarbons such as polyisobutylene, polybutenes, hydrogenated polydecenes, the polyglycols, including polypropylene glycol, polyethylene glycol, synthetic ester oils illustrated by trimethylolpropane esters, neopentyl alcohol and pentaerythritol esters, di(2-ethylhexyl) sebacate, di(2-ethylhexyl) adipate, dibutyl phthalate and other types, as for example, fluorocarbons, esters of phosphorus-containing acids, liquid ureas, ferrocene derivatives, hydrogenated synthetic oils, chain-type polyphenols, siloxanes and silicones (polysiloxanes), alkyl-substituted diphenyl esters typified by a butyl substituted bis (p-phenoxyphenyl) ether and phenoxyphenyl ether.

Having described the invention broadly, the following are offered as specific illustrations. They are illustrative only and are not intended to limit the invention.

EXAMPLE 1

GLYCEROL MONOOLEATE-DIMERCAPTOTHIADIAZOLE ADDUCT

Approximately 200 g of a commercial glycerol monooleate (60/40-glycerol monooleate/glycerol dioleate) and 30 g of 2,5-dimercapto-1,3,4-thiadiazole were charged to a stirred reactor and heated to 200° C. with agitation for 7½ hours under a nitrogen atmosphere. The product was cooled to 100° C. and filtered over diatomaceous earth. The adduct was a brown fluid and contained:
2.8% nitrogen
8.5% sulfur
68.0% carbon
9.8% hydrogen

EXAMPLE 2

BORATED GLYCEROL MONOOLEATE-DIMERCAPTOTHIADIAZOLE ADDUCT

Approximately 2000 g of borated glycerol monooleate (prepared by the boric acid treatment of glycerol monooleate) and 250 g of 2,5-dimercapto-1,3,4-thiadiazole were charged to a stirred reactor and heated to 180° C. with agitation for five hours under a nitrogen atmosphere. The product was cooled to 100° C. and filtered over diatomaceous earth. The adduct was a brown fluid and contained:
- 1.6% boron
- 2.1% nitrogen
- 6.3% sulfur
- 64.9% carbon
- 9.9% hydrogen

EXAMPLE 3

BORATED GLYCEROL MONOOLEATE-DIMERCAPTOTHIADIAZOLE ADDUCT

Approximately 160 g of borated glycerol monooleate (prepared by the boric acid treatment of glycerol monooleate) and 20 g of 2,5-dimercapto-1,3,4-thiadiazole were charged to a reactor and heated at 180°–190° C. with agitation for 4½ hours under a nitrogen atmosphere. The product was cooled to 100° C. and filtered over diatomaceous earth. The adduct was a brown fluid and contained:
- 2.3% nitrogen
- 6.5% sulfur
- 67.1% carbon
- 9.7% hydrogen

EXAMPLE 4

PENTAERYTHRITOL TRIOLEATE-DIMERCAPTOTHIADIAZOLE ADDUCT

Approximately 345 g of pentaerythritol trioleate (prepared by the reaction of one mole of pentaerythritol with three moles of oleic acid) and 30 g of 2,5-dimercapto-1,3,4-thiadiazole were charged to a stirred reactor and heated to 180°–200° C. for 4 hours under a nitrogen atmosphere. The product was cooled to 100° C. and filtered over diatomaceous earth. The product was an oil soluble clear brown fluid.

EXAMPLE 5

BORATED PENTAERYTHRITOL TRIOLEATE-DIMERCAPTOTHIADIAZOLE ADDUCT

Approximately 2000 g of borated pentaerythritol trioleate (prepared by the reaction of boric acid with pentaerythritol trioleate) and 175 g of 2,5-dimercapto-1,3,4-thiadiazole were charged to a stirred reactor and heated at 180° C. for 5 hours under a nitrogen atmosphere. The product was cooled to 100° C. and filtered over diatomaceous earth. The product was a clear brown oil soluble fluid.

Each of the above examples was then individually incorporated into a fully formulated 5W-20 automotive engine oil having the following general characteristics: KV at 100° C.-6.8 cs; KV at 40° C.-36.9 cs; VI -143 and evaluated using the Low Velocity Friction Apparatus.

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever cam-motor arrangement.

Procedure

The rubbing surfaces and 12–13 ml. of test lubricant are placed on the LVFA. A 500 psi load is applied, and the sliding speed is maintained at 30 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 4 to 8 microinches. The percentages by weight are percentages by weight of the total lubricating oil composition, including the usual additive package. The data are percent decrease in friction according to:

$$\frac{(U_k \text{ of oil alone}) - (U_k \text{ of Additive plus oil}) \times 100}{(U_k \text{ of oil alone})}$$

The value for the oil alone would be zero as shown in the Table below.

Table 1 summarizes the results.

TABLE 1

FRICTION REDUCTION TEST RESULTS

| Example | Additive Conc. Wt. % | Percent Change in Coefficient of Friction | |
|---|---|---|---|
| | | 5 Ft./Min. | 30 Ft./Min. |
| | — | 0 | 0 |
| 1 | 4 | 26 | 25 |
| 2 | 4 | 24 | 24 |
| 3 | 4 | 29 | 29 |
| 4 | 4 | 25 | 19 |
| 5 | 4 | 27 | 21 |

Using a solvent paraffinic neutral mineral oil, copper corrosivity tests were run in accordance with ASTM D130-6 and ASTM D130-9. Table 2 shows the results.

TABLE 2

COPPER STRIP CORROSIVITY

| Example | Additive Conc., WT. % | ASTM D130-6 210° F., 6 Hrs. | ASTM D130-9 250° F., 3 Hrs. |
|---|---|---|---|
| 1 | 1 | 1B | 1B |
| | 3 | 1B | 1B |
| 2 | 1 | 1B | 1A |
| | 3 | 1A | 1A |
| 4 | 1 | 1B | 1A |
| | 3 | 1B | 1B |
| 5 | 1 | 1A | 1A |

TABLE 2-continued

| | COPPER STRIP CORROSIVITY | | |
|---|---|---|---|
| Example | Additive Conc., WT. % | ASTM D130-6 210° F., 6 Hrs. | ASTM D130-9 250° F., 3 Hrs. |
| | 3 | 1A | 1A |

We claim:

1. A product of reaction obtained by reacting at a temperature of from about 140° C. to about 200° C. a hydroxyl-containing unsaturated ester or a borated derivative thereof with a mercaptothiadiazole.

2. The product of claim 1 wherein the hydroxyl-containing ester is obtained by reacting an unsaturated monocarboxylic acid of the formula

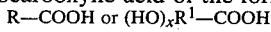
R—COOH or (HO)$_x$R$^1$—COOH wherein R is an alkenyl group containing 2 to 30 carbon atoms, R$^1$ is an alkenylene group containing 2 to 20 carbon atoms and x is 1 to 3, with a polyhydric alcohol containing from 2 to 30 carbon atoms and from 2 to 6 hydroxyl groups.

3. The product of claim 2 wherein the boron compound used for boration is boric acid or has the formula

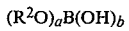
(R$^2$O)$_a$B(OH)$_b$ wherein R$^2$ is a C$_1$-C$_6$ alkyl group, a is 1 to 3 and b is 0 to 2.

4. The product of claim 2 wherein the mercaptothiadiazole has the formula:

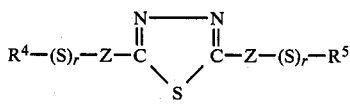

wherein R$^4$ and R$^5$ are hydrogen or hydrocarbyl groups containing from 1 to 30 carbon atoms, r is 0 to 3 and z is nitrogen or sulfur, and wherein either R$^4$ or R$^5$ must be hydrogen and at least one Z must be sulfur.

5. The product of claim 4 wherein said hydrocarbyl groups are alkyl, aryl, alkenyl, alkaryl or aralkyl groups.

6. The product of claim 1 obtained by reacting glycerol monooleate with 2,5-dimercapto-1,3,4-thiadiazole.

7. The product of claim 1 obtained by reacting borated glycerol monooleate with 2,5-dimercapto-1,3,4-thiadiazole.

8. The product of claim 3 wherein boration is with boric acid.

9. The product of claim 1 obtained by reacting pentaerythritol trioleate with 2,5-dimercapto-1,3,4-thiadiazole.

10. The product of claim 1 obtained by reacting borated pentaerythritol trioleate with 2,5-dimercapto-1,3,4-thiadiazole.

11. The product of claim 10 wherein boration is with boric acid.

12. A lubricant composition containing a major amount of a lubricant selected from the group consisting of oils of lubricating viscosity and greases thereof and a friction reducing amount of a product of reaction obtained by reacting a hydroxyl-containing unsaturated ester or a borated derivation thereof with a mercaptothiadiazole said reaction obtained at a temperature of from about 140° C. to about 200° C.

13. The composition of claim 12 wherein in preparing said product the hydroxyl-containing ester is obtained by reacting an unsaturated monocarboxylic acid of the formula

R—COOH or (HO)$_x$—R$^1$—COOH wherein R is an alkenyl group containing 2 to 30 carbon atoms, R$^1$ is an alkenylene group containing 2 to 20 carbon atoms and x is 1 to 3, with a polyhydric alcohol containing 2 to 30 carbon atoms and 2 to 6 hydroxyl groups.

14. The composition of claim 13 wherein in preparing said product the boron compound used for boration is boric acid or has the formula

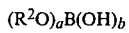
(R$^2$O)$_a$B(OH)$_b$ wherein R$^2$ is a C$_1$-C$_6$ alkyl group, a is 1 to 3 and b is 0 to 2.

15. The composition of claim 13 wherein in preparing said product, the mercaptothiadiazole has the formula

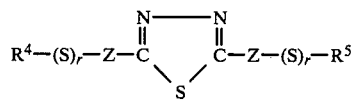

wherein R$^4$ and R$^5$ are hydrogen or hydrocarbyl groups containing from 1 to 30 carbon atoms, r is 0 to 3 and Z is nitrogen or sulfur, and wherein either R$^4$ or R$^5$ must be hydrogen and at least one Z must be sulfur.

16. The composition of claim 15 wherein said hydrocarbyl groups are alkyl, aryl, alkenyl alkaryl or aralkyl groups.

17. The composition of claim 12 wherein said product is prepared by reacting glycerol monooleate with 2,5-dimercapto-1,3,4-thiadiazole.

18. The composition of claim 12 wherein said product is prepared by reacting borated glycerol monooleate with 2,5-dimercapto-1,3,4-thiadiazole.

19. The composition of claim 14 wherein boration is with boric acid.

20. The composition of claim 12 wherein said product is prepared by reacting pentaerythritol trioleate with 2,5-dimercapto-1,3,4-thiadiazole.

21. The composition of claim 12 wherein said product is prepared by reacting borated pentaerythritol trioleate with 2,5-dimercapto-1,3,4-thiadiazole.

22. The composition of claim 21 wherein boration is with boric acid.

23. The composition of claim 12 wherein said lubricant is a mineral oil.

24. The composition of claim 12 wherein said lubricant is a synthetic oil.

25. The composition of claim 12 wherein said lubricant is a mixture of mineral and synthetic oils.

26. The composition of claim 12 wherein said lubricant is a grease prepared from a mineral oil, a synthetic oil or a mixture thereof.

* * * * *

UNITED STATES PATENT AND TRADEMARK OFFICE
CERTIFICATE OF CORRECTION

PATENT NO. : 4,301,019
DATED : November 17, 1981
INVENTOR(S) : ANDREW G. HORODYSKY and PHILIP S. LANDIS It is certified that error appears in the above–identified patent and that said Letters Patent are hereby corrected as shown below:

Column 2, line 54, "gnerally" should be --generally--.

Column 9, line 39, little "z" should be capitalized --Z--.

Signed and Sealed this

Seventh Day of December 1982

[SEAL]

Attest:

Attesting Officer

GERALD J. MOSSINGHOFF
Commissioner of Patents and Trademarks